(12) United States Patent
Roh et al.

(10) Patent No.: US 9,448,199 B2
(45) Date of Patent: Sep. 20, 2016

(54) APPARATUS AND METHOD FOR DETERMINING BATTERY CURRENT CONSUMPTION IN A PORTABLE TERMINAL

(71) Applicant: Samsung Electronics Co., Ltd, Gyeonggi-do (KR)

(72) Inventors: Young-Gil Roh, Gyeonggi-do (KR); Jong-Woo Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 664 days.

(21) Appl. No.: 13/661,829

(22) Filed: Oct. 26, 2012

(65) Prior Publication Data

US 2013/0119998 A1    May 16, 2013

(30) Foreign Application Priority Data

Oct. 28, 2011 (KR) .......................... 10-2011-0111505

(51) Int. Cl.
*G01N 27/416* (2006.01)
*G01R 31/36* (2006.01)

(52) U.S. Cl.
CPC ......... *G01N 27/416* (2013.01); *G01R 31/3651* (2013.01); *G01R 31/362* (2013.01)

(58) Field of Classification Search
USPC ........................................................ 324/427
See application file for complete search history.

(56) References Cited

U.S. PATENT DOCUMENTS

| 5,811,890 A * | 9/1998 | Hamamoto ........ G01R 31/3648 307/66 |
|---|---|---|
| 2008/0158390 A1* | 7/2008 | Chuang .................... 348/231.99 |
| 2009/0237033 A1* | 9/2009 | Kanzaki et al. .............. 320/134 |
| 2010/0250164 A1 | 9/2010 | Zheng et al. |

FOREIGN PATENT DOCUMENTS

KR    10-2006-0073212    6/2006

* cited by examiner

*Primary Examiner* — Robert Grant

(57) ABSTRACT

According to one embodiment, an apparatus for selecting a battery voltage table including current consumption information of applications, and applying an offset to a battery output voltage according to current consumption of applications. The apparatus for determining a battery status in a portable terminal includes a memory unit configured to store a battery voltage table defined according to current consumption, a control unit configured to determine an executed application, and a power estimation unit configured to estimate a battery level using the battery voltage table defined for each current consumption of applications and a battery output voltage.

14 Claims, 7 Drawing Sheets

APPARATUS AND METHOD FOR DETERMINING BATTERY CURRENT CONSUMPTION IN A PORTABLE TERMINAL

CROSS-REFERENCE TO RELATED APPLICATION(S) AND CLAIM OF PRIORITY

The present application is related to and claims priority under 35 U.S.C. §119 to an application filed in the Korean Intellectual Property Office on Oct. 28, 2011 and assigned Serial No. 10-2011-0111505, the contents of which are incorporated herein by reference.

TECHNICAL FIELD OF THE INVENTION

The present invention relates generally to battery powered devices, and more particularly, to an apparatus and method for determining battery current consumption in a portable terminal.

BACKGROUND OF THE INVENTION

The use of portable terminals has increased due to their portability. Thus, terminal manufacturers have competitively developed portable terminals with more convenient functions in order to attract more users. For example, portable terminals now typically provide various functions such as phone books, games, schedulers, short message services, multimedia message services, Internet service, e-mail service, wake-up calling, MPEG Audio Layer-3 (MP3) players, and digital cameras.

In order to provide portability, portable terminals typically use a detachable rechargeable battery as a power supply. Due to a limited capacity of the rechargeable battery, users of the portable terminal are often required to check a rechargeable battery level and charge the rechargeable battery by using an external power supply.

The portable terminals display a battery level indication bar on its display screen so that users can easily recognize a current battery level. The battery level indication bar includes a plurality of bars, and the number of bars gradually decreases with an increase in battery consumption to inform the user of the time when the rechargeable battery is completely consumed.

In general, a portable terminal has a battery gauge to monitor a battery level.

When a battery gauge is used, a battery level can be exactly detected. However, the battery gauge and a circuit for operating the battery gauge causes an increase in the unit price of a portable terminal.

In order to overcome the above problem, a portable terminal estimates a battery level by measuring a battery output voltage, instead of by use of a battery gauge. That is, the portable terminal estimates a battery level by predefining and prestoring a battery level for each battery output voltage in a battery voltage table and measuring an output voltage. Although this technique may be less expensive, when the battery output voltage is used, the accuracy may be low compared to using the battery gauge. Nevertheless, when an application with relatively high current consumption is executed in a portable terminal, a voltage across a battery drops due to this increase in current consumption. As a result, when a battery level is estimated using a battery output voltage, a battery level lower than a current battery level is estimated.

Therefore, there is a need for an apparatus and method for improving the performance of a battery level estimation using a battery output voltage in a portable terminal.

SUMMARY OF THE INVENTION

To address the above-discussed deficiencies of the prior art, it is a primary object to provide an apparatus and method for improving the performance of a battery level estimation in a portable terminal.

Another object of the present invention is to provide an apparatus and method for detecting a battery level using current consumption of an application executed in a portable terminal.

Another object of the present invention is to provide an apparatus and method for selecting a battery voltage table according to the current consumption of an application in a portable terminal.

Another object of the present invention is to provide an apparatus and method for applying an offset to a battery output voltage according to the current consumption of an application in a portable terminal.

According to an aspect of the present invention, an apparatus for determining a battery status in a portable terminal includes a memory unit configured to store a battery voltage table including current consumption information. a control unit configured to determine an executed application; and a power estimation unit configured to estimate a battery level using the current consumption information of the executed applications and a battery output voltage, wherein the battery voltage table is a table that defines a battery level for each battery output voltage.

According to another aspect of the present invention, a method for determining a battery status in a portable terminal includes defining a battery voltage table that includes current consumption information of applications; loading a battery voltage table corresponding to the current consumption upon execution of the application; and estimating a battery level using the battery output voltage and the loaded battery voltage table.

According to another aspect of the present invention, an electronic device includes at least one processor, a memory, and at least one module stored in the memory and executed by the at least one processor, wherein information associated with the module is included in a battery voltage table that includes current consumption information of applications, loads the battery voltage table corresponding to the current consumption upon execution of the application, and estimates a battery level using the battery output voltage and the loaded battery voltage table.

Before undertaking the DETAILED DESCRIPTION OF THE INVENTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION OF THE INVENTION

FIGS. 1 through 6, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged battery powered devices. Exemplary embodiments of the present invention will be described herein below with reference to the accompanying drawings. In the following description, detailed descriptions of well-known functions or configurations will be omitted since they would unnecessarily obscure the subject matters of the present invention.

An apparatus and method for improving performance of a detection level of a battery by using current consumption of an application in a portable terminal will be described below. The portable terminal refers to a generic portable electronic device. Examples of the portable terminal include a mobile phone, a media player, a tablet computer, a handheld computer, and a personal digital assistant (PDA). Also, the portable terminal may be any portable electronic device including a combination of two or more functions of the above-mentioned devices.

Figure 1:
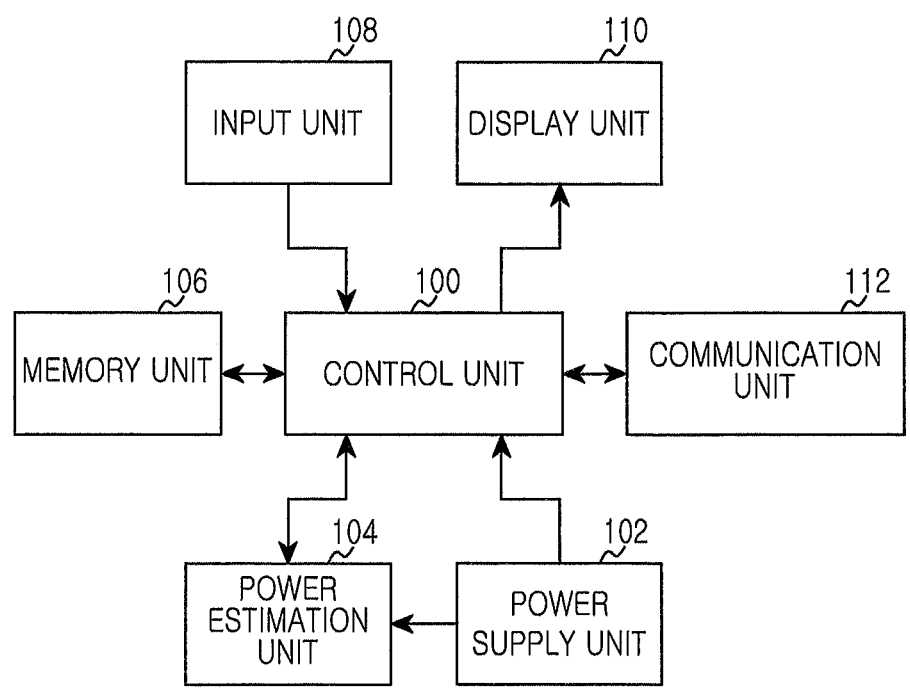
FIG. 1 illustrates an example portable terminal configured to detect a battery level according to embodiments of the present invention.

FIG. 1 illustrates an example portable terminal configured to detect a battery level according to embodiments of the present invention.

Referring to FIG. 1, the portable terminal may include a control unit 100, a power supply unit 102, a power estimation unit 104, a memory unit 106, an input unit 108, a display unit 110 and a communication unit 112.

The control unit 100 of the portable terminal controls an overall operation of the portable terminal. For example, the control unit 100 performs a processing and control for voice call and data communication. In addition to the general functions, according to the present invention, the control unit 100 groups pre-installed applications according to current consumption, and sets a battery voltage table for each group.

Also, the control unit 100 loads a battery voltage table corresponding to current consumption of an executed application and detects a battery level.

That is, after measuring a battery output voltage, the control unit 100 compares the measured result with the battery voltage table corresponding to the application and estimates a current battery level.

In addition, in order to estimate a battery level according to the current consumption of the executed application, the control unit 100 determines that the battery output voltage has been measured in a situation in which no current is consumed, such that an offset may be applied to the measured battery output voltage.

The operations of the control unit 100 may be executed by software (instruction set) stored in the memory. The software may be executed by the control unit 100.

The power supply unit 102 includes a battery. The battery is rechargeable and detachable from the portable terminal, and supplies power received from the battery to each component of the portable terminal.

That is, the power supply unit 102 supplies operational power received from the battery to each component when the power of the portable terminal is turned on, and charges the battery when charging power is supplied from an external power supply.

The power estimation unit 104 loads the battery voltage table corresponding to the executed application and detects a battery level.

For example, the power estimation unit 104 determines a group to which the executable application belongs, and loads a battery voltage table including a rated current consumption of applications in the determined group.

The application may be set to a plurality of groups according to current consumption, and the battery voltage table includes information associated with battery levels for each battery output voltage. The power estimation unit 104 manages the battery voltage table corresponding to each group.

The power estimation unit 104 that loads the battery voltage table corresponding to the group of the executed application as above measures an output voltage of the power supply unit 102, and compares the measured output voltage with the battery voltage table to estimate a current battery level.

A conventional portable terminal does not use a battery voltage table corresponding to current consumption of applications. Hence, when an application with a relatively high level of current consumption is executed, a voltage across the battery drops and thus the detected battery level of the conventional portable terminal may be incorrect. However, certain embodiments of the portable terminal can solve the problems of the conventional portable terminal by using a battery voltage table corresponding to current consumption of an executed application.

The operations of the power supply unit 102 and the power estimation unit 104 may be executed by a specific module (instruction set) stored in the memory unit 106.

The memory unit 106 includes a ROM, a RAM and a flash ROM. The ROM stores various reference data and microcodes of programs for processing and controlling the control unit 100 and the power estimation unit 104.

The RAM is a working memory of the control unit 100, which stores temporary data generated during the execution of various programs. Also, the flash ROM stores various updatable backup data such as phone book, outgoing messages, and incoming messages.

In addition, the memory unit 106 stores group information of applications grouped depending on current consumption, and stores a battery voltage table corresponding to a type or group of the executed application. Furthermore, the memory unit 106 stores information on current consumption of an application installed in the portable terminal in order to check the battery voltage table of the application.

According to the present invention, the memory unit 106 stores a software module for performing operations of the control unit 100, the power supply unit 102, and the power estimation unit 104.

The input unit 108 includes numeric keys of 0-9 and a plurality of function keys, such as a Menu key, a Cancel (Delete) key, a Confirmation (OK) key, a Talk (Call) key, an End key, an Internet connection key, Navigation keys (or Direction keys), and character input keys. The input unit 108 provides the control unit 100 with key input data that corresponds to a key pressed by the user. According to the present invention, the input unit 108 provides the control unit 100 with key input data for executing an application.

The display unit 110 displays numerals and characters, moving pictures, still pictures, and status information generated during the operation of the portable terminal. The display unit 110 may include a color liquid crystal display (LCD), an active-matrix organic light-emitting diode (AMOLED) display, or the like. If the display unit 110 has a touch input device and is applied to a touch input type portable terminal, it may be used as an input device.

In fact, it is within the spirit and scope of the presently claimed invention that the input unit 108 and display unit 110 could all be served by a single touch screen. That is, a touch sensitive display, called as a touch screen, may be used as the display unit 110. In this situation, touch input may be performed via the touch sensitive display.

The communication unit 112 transmits/receives Radio Frequency (RF) signals inputted/outputted through an antenna (not illustrated). For example, in a transmitting (TX) mode, the communication unit 112 channel-encodes, spreads and RF-processes TX data prior to transmission. In a receiving (RX) mode, the communication unit 112 converts a received RF signal into a baseband signal and despreads and channel-decodes the baseband signal to restore the original data.

The above configurations should be considered in descriptive sense only and not for the purpose of limitation, and those skilled in the art will understand that various changes may be made therein without departing from the scope of the present invention. For example, although the power estimation unit 104 is provided and illustrated separately, the control unit 100 may be configured to perform all or some of the functions of the power estimation unit 104.

Figure 2:
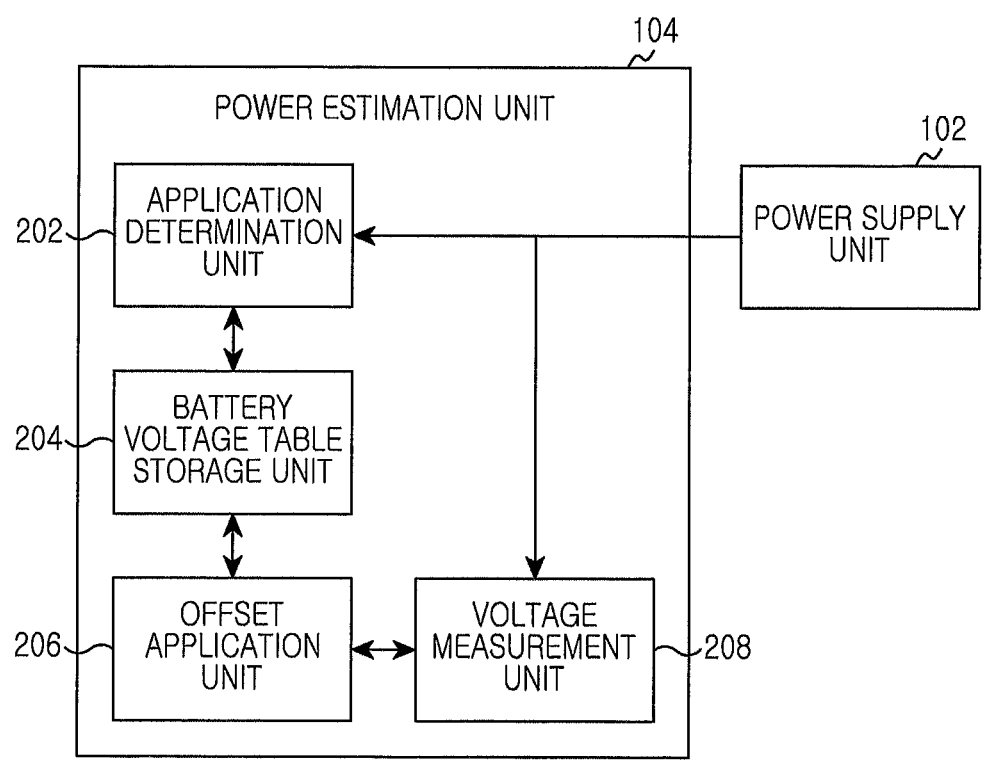
FIG. 2 illustrates an example configuration of a power estimation unit according to an embodiment of the present invention.

FIG. 2 illustrates an example power estimation unit according to an embodiment of the present invention.

Referring to FIG. 2, the power estimation unit 104 loads a battery voltage table corresponding to an executed application, detects a battery level, and applies an offset to a battery output voltage according to current consumption of the executed application. The power estimation unit 104 may include an application determination unit 202, a battery voltage table storage unit 204, an offset application unit 206, and a voltage measurement unit 208.

First, the power estimation unit 104 operates with power supplied from the power supply unit 102. The application determination unit 202 of the power estimation unit 104 determines a type of an application executed upon a request from a user.

The application determination unit 202 detects current consumption upon the execution of the application. For example, the application determination unit 202 may store information on current consumption for each installed application and detect the current consumption of the executed application.

In addition, the application determination unit 202 monitors an output voltage of the power supply unit (battery) upon the execution of the application, detects current consumption of the executed application, and determines whether an application with high current consumption is executed.

The battery voltage table storage unit 204 may store a table defining a battery level for each battery output voltage, and the battery voltage table may information associated with multiple battery levels depending on the application or current consumption of the application.

The voltage measurement unit 208 measures an output voltage of the power supply unit 102 such as a battery, and the offset application unit 206 applies an offset to the output voltage measured by the voltage measurement unit 208. That is, when an application with relatively high current consumption is executed, the offset application unit 206 applies an offset to the output voltage measured by the voltage measurement unit 208. Additionally, the offset application unit 206 may apply another offset, or no offset, when no current is consumed by any application.

Figure 3:
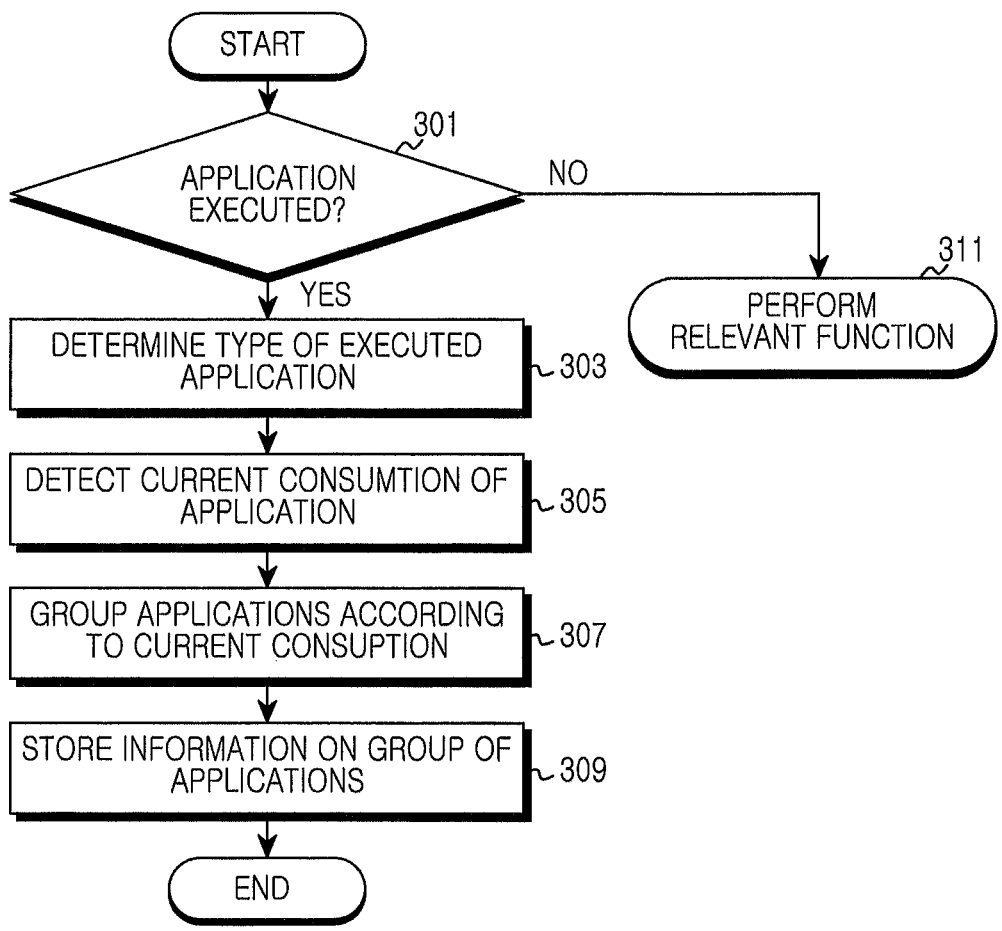
FIG. 3 illustrates an example process for grouping applications according to current consumption in a portable terminal according to an embodiment of the present invention.

FIG. 3 illustrates an example process for grouping applications depending on current consumption in a portable terminal according to an embodiment of the present invention.

Referring to FIG. 3, the portable terminal groups and stores applications depending on current consumption in order to select a battery voltage table to be used to detect a battery level of the portable terminal.

First, the portable terminal determines whether an application is executed in step 301.

When it is determined in step S301 that no application is executed, the portable terminal proceeds to step 311 to perform a relevant function (e.g., a standby mode).

On the other hand, when it is determined in step S301 that an application is executed, the portable terminal proceeds to step 303 to determine a type of the executed application, and proceeds to step 305 to detect current consumption of the application. Since the portable terminal stores information on current consumption for each installed application, the portable terminal may detect the current consumption of the executed application. Furthermore, the portable terminal may monitor a battery output voltage upon the execution of the application, and detect the current consumption of the executed application. Thereafter, the portable terminal proceeds to step 307 to group applications depending on current consumption, and proceeds to step 309 to store information on the grouped applications.

For example, the portable terminal may group applications depending on current consumption as shown in Table 1 below, and may change a battery voltage table depending on a type of an executed application. As shown, the battery voltage table includes information that defines a battery level for each battery output voltage.

TABLE 1

| Group | Executed Application |
| --- | --- |
| Group 1 (below 150 mA) | MP3, LCD ON |
| Group 2 (150 mA~250 mA) | Camera, Motion Regeneration |
| Group 3 (250 mA~400 mA) | Wi-Fi, GPS |
| Group 4 (above 400 mA) | Video Photographing, Internet |

The portable terminal may classify and group applications according to a current consumption of 150 mA or less, 250 mA or less, 400 mA or less, and 400 mA or more.

Thereafter, the portable terminal ends the algorithm.

Figure 4:
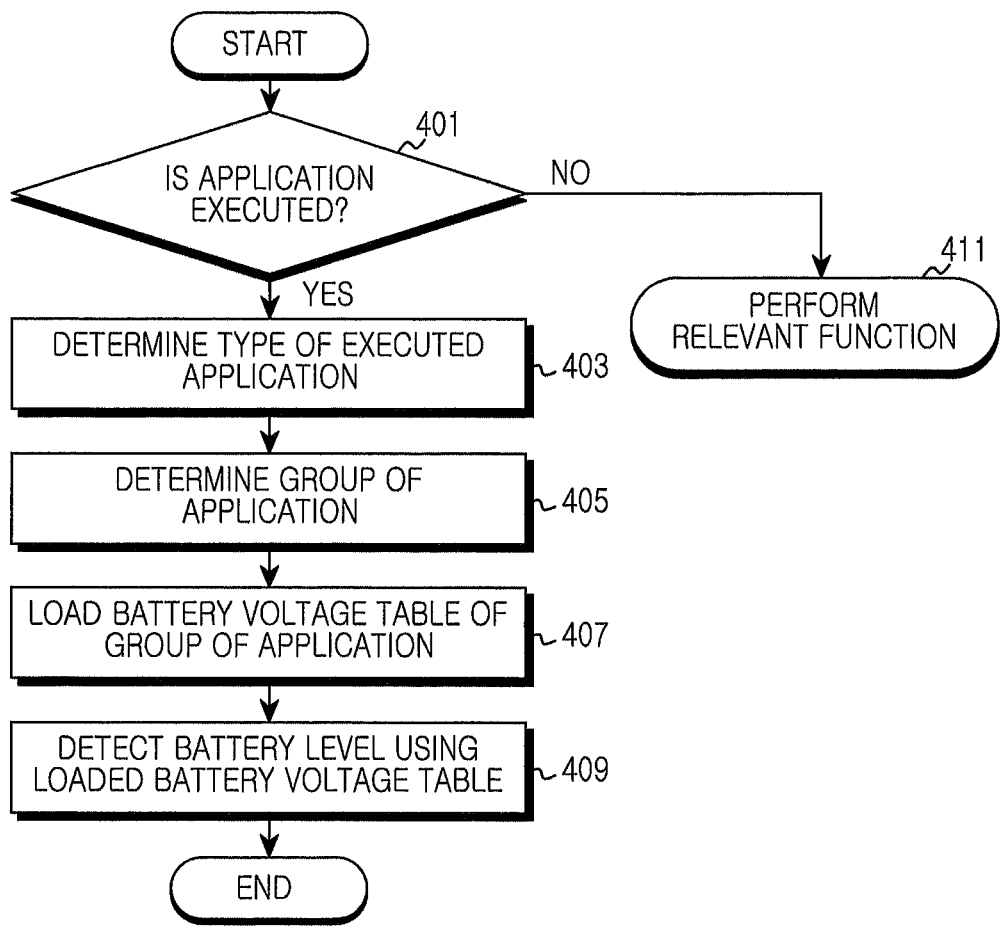
FIG. 4 illustrates an example process for detecting a battery level in a portable terminal according to an exemplary embodiment of the present invention.

FIG. 4 illustrates an example process for detecting a battery level in a portable terminal according to an embodiment of the present invention.

Referring to FIG. 4, the portable terminal stores a battery voltage table defined according to current consumption of multiple applications, and selects the battery voltage table according to a particular executed application.

First, the portable terminal determines whether an application is executed in step 401.

When it is determined in step S401 that no application is executed, the portable terminal proceeds to step 311 to perform a relevant function (e.g., a standby mode).

Meanwhile, when it is determined in step S401 that an application is executed, the portable terminal proceeds to step 403 to determine a type of the executed application.

Then, the portable terminal proceeds to step 405 to determine a group to which the executed application belongs, and proceeds to step 407 to load a battery voltage table corresponding to the group to which the executed application belongs. That is, since the portable terminal performs the operations as illustrated in FIG. 3, groups applications according to current consumption, and stores information on the groups, the portable terminal may determine the group to which the executed application belongs.

Thereafter, the portable terminal proceeds to step 409, and detects a battery level using the loaded battery voltage table. The battery voltage table includes information associated with a battery level for each battery output voltage.

When an application with relatively high current consumption is executed in detecting a battery level using a generic battery voltage table and a battery output voltage, the battery level may not be detected properly. To solve this problem, a battery voltage table corresponding to the current consumption of an application is used.

In addition, when a battery voltage drops to a relatively large degree, the portable terminal may determine that an application having high current consumption is executed, and may use a battery voltage table corresponding to the current consumption.

Thereafter, the portable terminal ends the algorithm.

Figure 5:
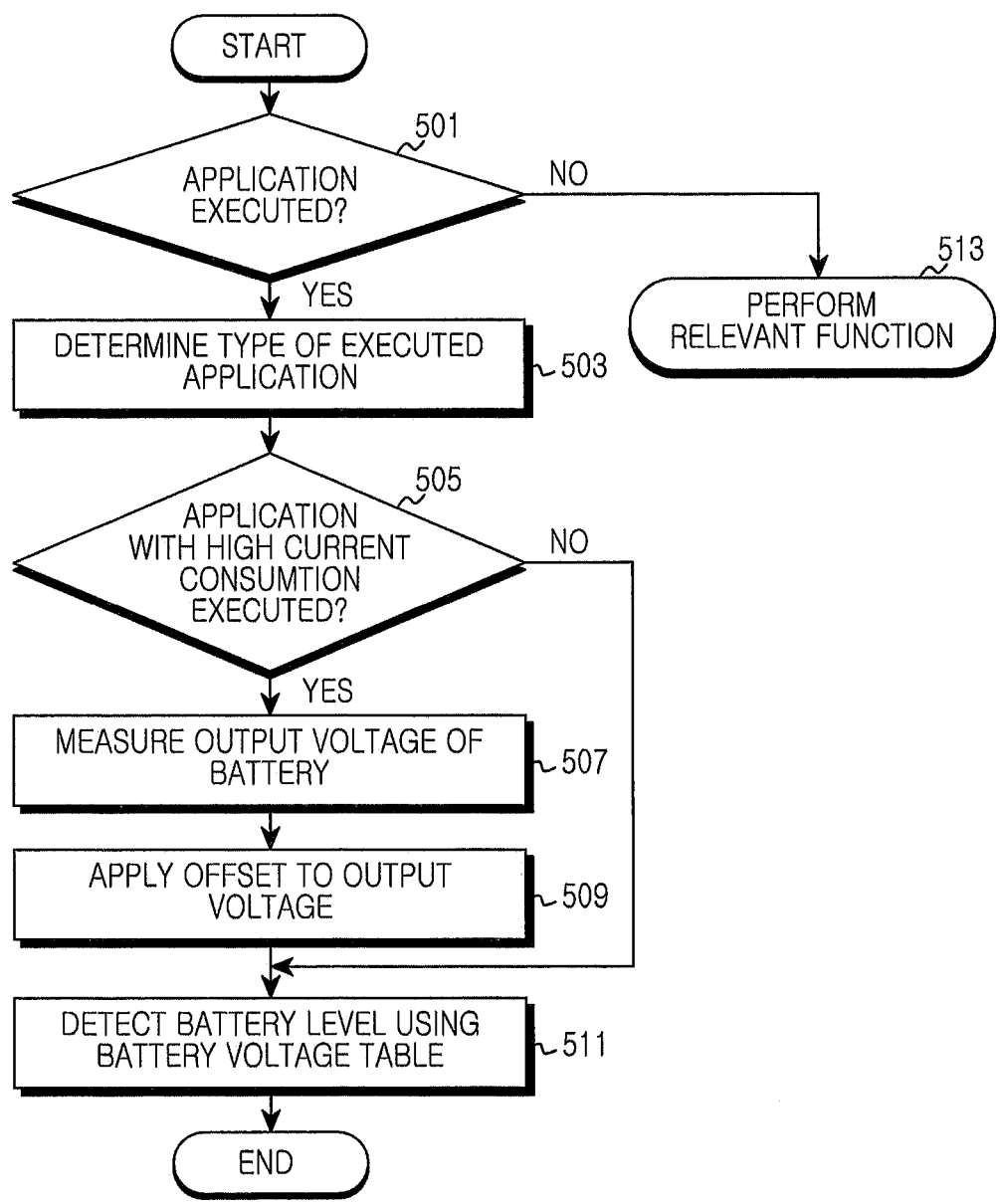
FIG. 5 illustrates an example process for detecting a battery level in a portable terminal according to another exemplary embodiment of the present invention.

FIG. 5 illustrates an example process for detecting a battery level in a portable terminal according to another embodiment of the present invention.

Referring to FIG. 5, the portable terminal stores a battery voltage table that defines a battery level for each battery output voltage, and applies an offset to a battery output voltage measured according to current consumption of an executed application.

First, the portable terminal determines whether an application is executed in step 501.

When it is determined in step S501 that no application is executed, the portable terminal proceeds to step 513 to perform a relevant function (e.g., a standby mode).

Meanwhile, when it is determined in step S501 that an application is executed, the portable terminal proceeds to step 503 to determine a type of the executed application.

Thereafter, the portable terminal proceeds to step 505, and determines whether an application with relatively high current consumption is executed. The portable terminal may store information on the current consumption of the installed applications, and detect the current consumption of the executed application.

Moreover, when a battery voltage drops a relatively large degree, the portable terminal may determine that an application with high current consumption is executed.

One the other hand, when it is determined in step S505 that an application with a relatively low current consumption is executed, the portable terminal proceeds to step 511 to detect a battery level using a battery voltage table. That is, after measuring a battery output voltage, the portable terminal performs a general operation of detecting the battery level corresponding to the measured output voltage in the battery voltage table.

Meanwhile, when it is determined in step S505 that an application with relatively high current consumption is executed, the portable terminal proceeds to step 507 to measure a battery output voltage, and proceeds to step 509 to apply an offset to the measured battery output voltage. In one embodiment, the applied offset may be proportional to the current consumption of the executed application.

In this case, the portable terminal may apply an offset of a constant value or an offset for each interval to an output voltage for each battery level. For example, the same offset may be applied to an output voltage corresponding to 100% to 0% of a battery level, or a different offset may be applied for each interval.

Then, the portable terminal proceeds to step 511 to detect a battery level using the battery voltage table.

That is, the portable terminal uses a battery voltage table that shows a battery level of 50% when a battery output voltage is 3.801 V and shows a battery level of 20% when a battery output voltage is 3.738 V. When assuming that a current battery output voltage is 3.801 V, an output voltage measured in a situation in which no application is executed is 3.801 V. Therefore, the portable terminal exactly measures a battery level as 50%.

However, when an application with relatively high current consumption, such as video shooting, is executed in the portable terminal, a battery output voltage may be measured to be 3.746 V, and a battery level of 50% is determined to be slightly over 20%.

Therefore, when an application with relatively high current consumption is executed, an offset is applied to a measureable output voltage of 3.746 V. Thus, the portable terminal recognizes that a battery output voltage corresponding to a voltage of 3.801 V is measured, and determines that a battery level is 50%.

Thereafter, the portable terminal ends the algorithm.

Figure 6A:
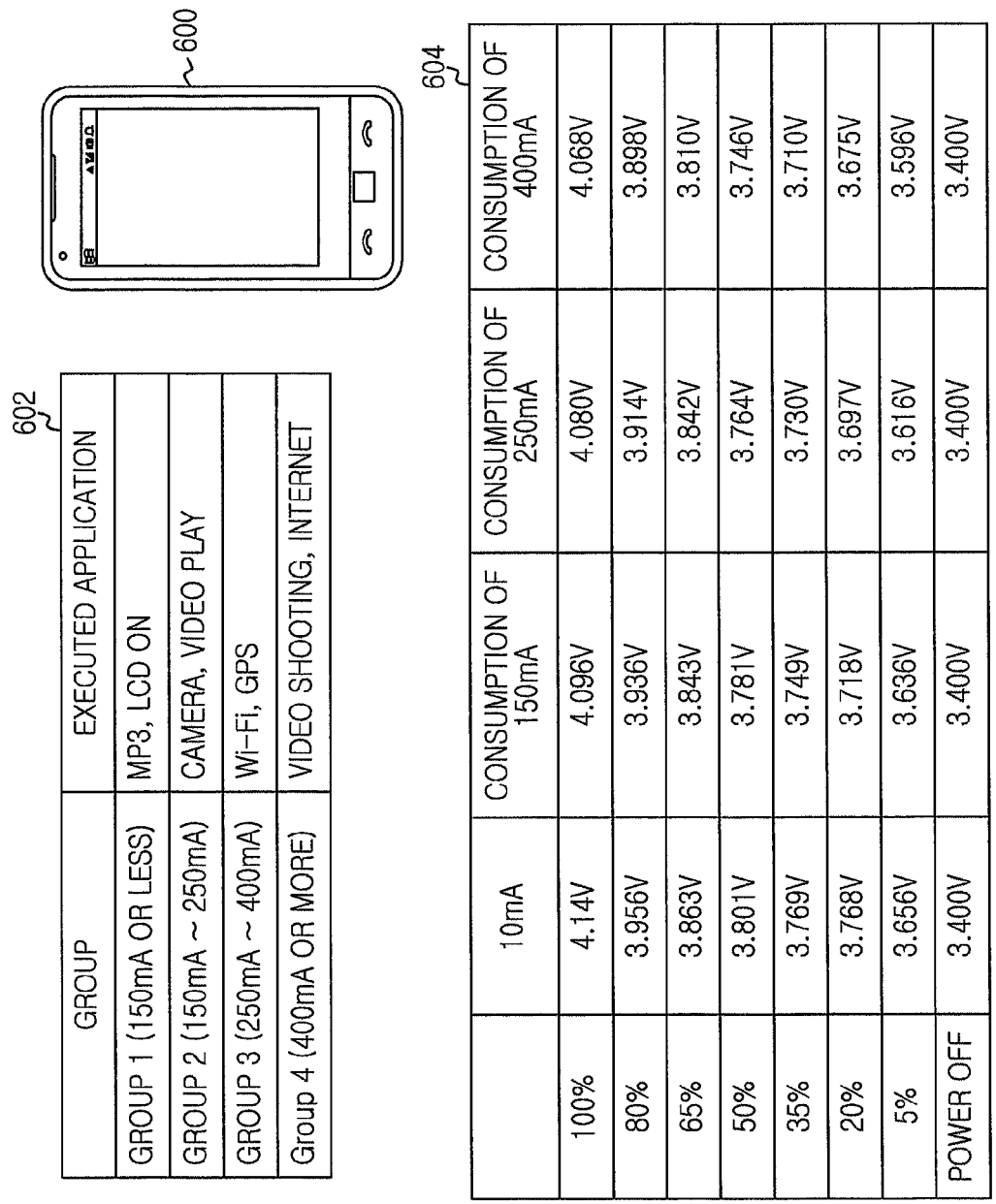
FIGS. 6A and 6B illustrate an example process for changing a battery voltage table according to execution of an application in a portable terminal according to an embodiment of the present invention.
Figure 6B:
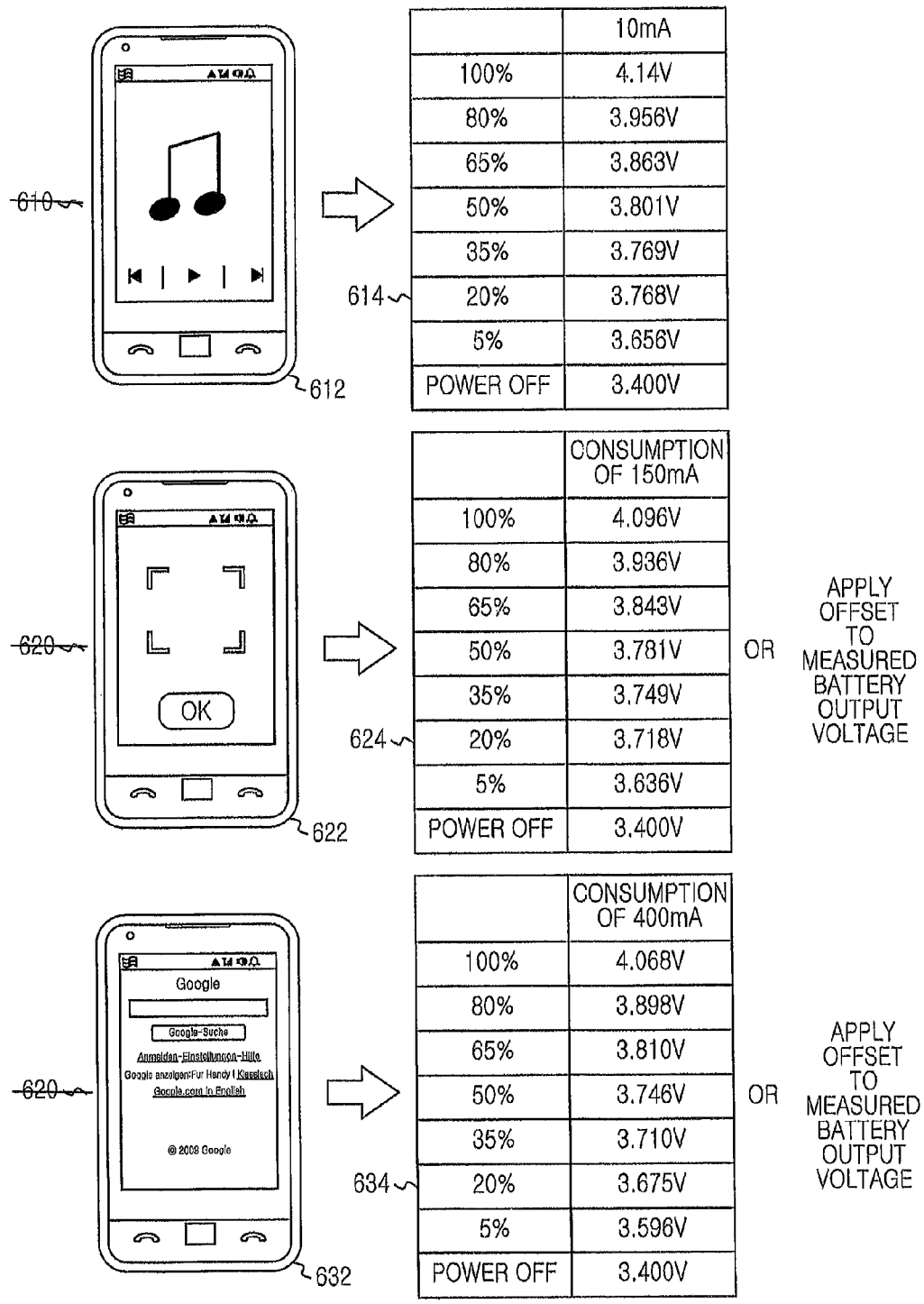

FIGS. 6A and 6B illustrate an example process for selecting a battery voltage table according to execution of an application in a portable terminal according to an embodiment of the present invention.

Referring to FIG. 6A, a portable terminal 600 stores information 602 on applications grouped for current consumption in order to select a battery voltage table according to execution of the applications, and a battery voltage table 604 defined according the current consumption. The information 602 and the battery voltage table 604 are illustrated in FIG. 6A.

As a result, as illustrated in FIG. 6B, the portable terminal 600 may change the battery voltage table according to the current consumption of an executed application.

For example, when it is determined that a music play application (e.g., MP3 player) is executed in a portable terminal 612, the portable terminal 612 determines that a current consumption is 150 mA or less upon the execution of the music play application by using the prestored information on the grouped applications.

As a result, the portable terminal 612 determines that a current is not almost consumed upon the execution of the application, and uses a battery voltage table 614 used when a current consumption is 10 mA.

Meanwhile, when it is determined that a camera application is executed in a portable terminal 622, the portable terminal 622 determines that a current consumption is 150 mA to 250 mA upon the execution of the camera application by using the prestored information of the grouped applications, and determines that the execution of the camera application causes a voltage across the battery to drop.

Therefore, the portable terminal 622 uses a battery voltage table 624 used when a current consumption is 150 mA upon the execution of the camera application.

In addition, when it is determined that a web browser application is executed in a portable terminal 632, the portable terminal 632 determines that a current consumption is 400 mA or more upon the execution of the web browser application by using the prestored information on the grouped applications, and determines that the execution of the web browser application causes a voltage across the battery to drop.

Therefore, the portable terminal 632 uses a battery voltage table 634 used when a current consumption is 400 mA upon the execution of the web browser application.

When a battery voltage table corresponding to current consumption of an application does not exist, the portable terminal estimates a battery level using a battery voltage table showing the approximate current consumption of the application.

That is, in a portable terminal, a battery output voltage may be measured differently depending on the execution of an application.

For example, when an actual output voltage of a portable terminal is 3.90 V, an output voltage in an idle screen output state may be measured to be 3.90 V. However, when a camera application is executed, the current consumption of the application causes an actual battery output voltage of 3.90 V to be measured as 3.85 V, which may result in an error in a battery level detection. Therefore, a battery voltage table corresponding to the current consumption of the application is used.

In addition, the portable terminal according to another exemplary embodiment of the present invention applies an offset to the measured battery output voltage according to the current consumption of the application to recognize the output voltage as if the output voltage is measured in a situation in which no current is consumed. Therefore, certain embodiments of the portable terminal may detect a battery level to a relatively accurate degree.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

As described above, the performance of the battery level detection is improved by detecting a battery level by using current consumption of applications. Even though an application with high current consumption is executed, a battery level may be exactly estimated by changing a battery voltage table according to the current consumption of the executed application.

While the invention has been shown and described with reference to certain exemplary embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims, and all differences within the scope will be construed as being included in the present invention.

What is claimed is:

1. An apparatus configured to determine a battery status in an electronic device, the apparatus comprising:
   a memory unit configured to store a plurality of battery voltage tables, each of the plurality of battery voltage tables including a remaining battery level that corresponds to each of a plurality of battery output voltages of the electronic device, each of the plurality of battery voltage tables being set to be corresponding to each of a plurality of groups, the plurality of groups including one or more applications grouped according to a current consumed when an application is executed;
   a control unit configured to determine whether one or more applications are executed on the electronic device; and
   a power estimation unit configured to:
      identify, when the one or more applications are executed, the executed one or more applications,
      determine a group to which the identified one or more applications belong among the plurality of groups,
      select a battery voltage table corresponding to the determined group among the plurality of battery voltage tables, measure a battery output voltage, and
    estimate a remaining battery level using the measured battery output voltage and the selected battery voltage table.

2. The apparatus of claim 1, further comprising an offset application unit configured to apply an offset to the measured battery output voltage, wherein the power estimation unit is configured to estimate the remaining battery level using the offset-applied output voltage and the selected battery voltage table.

3. The apparatus of claim 2, wherein the offset is proportionally greater as the current increases.

4. The apparatus of claim 2, wherein the offset comprises at least one of a constant value and multiple offset values for each interval to an output voltage for each remaining battery level.

5. The apparatus of claim 1, wherein the electronic device comprises at least one of a mobile phone, a media player, a tablet computer, a handheld computer, and a personal digital assistant (PDA).

6. A method to determine a battery status in an electronic device, the method comprising:
defining a plurality of battery voltage tables, each of the plurality of battery voltage tables including a remaining battery level that corresponds to each of a plurality of battery output voltages of the electronic device, each of the plurality of battery voltage tables being set to be corresponding to each of a plurality of groups, the plurality of groups including one or more applications grouped according to a current consumed when an application is executed;
identifying, when one or more applications are executed, the executed one or more applications;
determining a group to which the identified one or more applications belong among the plurality of groups;
selecting a battery voltage table corresponding to the determined groups among the plurality of battery voltage tables;
measuring a battery output voltage; and
estimating a remaining battery level using the measured battery output voltage and the selected battery voltage table.

7. The method of claim 6, further comprising:
applying an offset to the measured battery output voltage; and
estimating a remaining battery level using the offset-applied battery output voltage and the selected battery voltage table.

8. The method of claim 7, wherein the offset is proportionally greater as the current increases.

9. The method of claim 7, wherein the offset comprises at least one of a constant value and multiple offset values for each interval to an output voltage for each remaining battery level.

10. The method of claim 7, wherein the electronic device comprises at least one of a mobile phone, a media player, a tablet computer, a handheld computer, and a personal digital assistant (PDA).

11. An electronic device, comprising:
at least one processor;
a memory configured to store a plurality of battery voltage tables, each of the plurality of battery voltage tables including a remaining battery level that corresponds to each of a plurality of battery voltages of the electronic device, each of the plurality of battery voltage tables being set to be corresponding to each of a plurality of groups, the plurality of groups including one or more applications grouped according to a current consumed when an application is executed; and
at least one module stored in the memory and executed by the at least one processor, wherein the module is configured to:
    identify, when one or more applications are executed, the executed one or more applications,
    determine a group to which the identified one or more applications belong among the plurality of groups,
    select a battery voltage table corresponding to the determined group among the plurality of battery voltage tables,
    measure a battery output voltage, and
    estimate a remaining battery level using the measured battery output voltage and the selected battery voltage table.

12. The device of claim 11, wherein the module is configured to measure a battery output voltage, apply an offset to the measured battery output voltage, and estimate a remaining battery level using the offset-applied battery output voltage and the battery voltage table.

13. The device of claim 12, wherein the offset is proportionally greater as the current increases.

14. The device of claim 12, wherein the offset comprises at least one of a constant value and multiple offset values for each interval to an output voltage for each remaining battery level.

\* \* \* \* \*